United States Patent
Lock et al.

(10) Patent No.: US 8,206,459 B1
(45) Date of Patent: Jun. 26, 2012

(54) PROSTHETIC-TO-LINER ATTACHMENT MECHANISM

(75) Inventors: Blair Lock, Chicago, IL (US); Todd Kuiken, Oak Park, IL (US); Robert Lipschutz, Naperville, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 182 days.

(21) Appl. No.: 12/406,720

(22) Filed: Mar. 18, 2009

(51) Int. Cl.
*A61F 2/78* (2006.01)
*A61F 2/80* (2006.01)
*A44B 1/04* (2006.01)
*A44B 1/02* (2006.01)

(52) U.S. Cl. ............ 623/33; 623/36; 24/303; 292/251.5

(58) Field of Classification Search .............. 623/32–38; 403/DIG. 1; 24/303; 292/251.5; 248/206.5, 248/309.4; 223/109 A, 120
See application file for complete search history.

(56) References Cited

U.S. PATENT DOCUMENTS

| | | | |
|---|---|---|---|
| 1,350,518 A * | 8/1920 | Prisbrey | 623/39 |
| 3,140,712 A | 7/1964 | Hunter | |
| 4,024,588 A | 5/1977 | Janssen et al. | |
| 4,112,941 A | 9/1978 | Larimore | |
| 4,536,898 A | 8/1985 | Palfray | |
| 4,743,264 A * | 5/1988 | Sherva-Parker | 623/33 |
| 4,908,037 A | 3/1990 | Ross | |
| 5,507,835 A | 4/1996 | Jore | |
| 5,879,386 A | 3/1999 | Jore | |
| 6,273,918 B1 | 8/2001 | Yuhasz et al. | |
| 6,387,096 B1 | 5/2002 | Hyde, Jr. | |
| 6,599,321 B2 | 7/2003 | Hyde, Jr. | |
| 6,705,794 B2 | 3/2004 | Varner et al. | |
| 7,033,400 B2 | 4/2006 | Currier | |
| 7,144,179 B2 | 12/2006 | Varner et al. | |
| 7,169,188 B2 | 1/2007 | Carstens | |
| 7,325,996 B2 | 2/2008 | Varner et al. | |
| 7,351,264 B2 | 4/2008 | Wilson | |
| 7,427,297 B2 | 9/2008 | Patterson et al. | |
| 2002/0032484 A1 | 3/2002 | Hyde, Jr. | |
| 2003/0187510 A1 | 10/2003 | Hyde | |
| 2003/0195633 A1 | 10/2003 | Hyde, Jr. | |
| 2003/0236572 A1 | 12/2003 | Bertram, III | |
| 2006/0096070 A1 * | 5/2006 | Ishida | 24/303 |
| 2006/0293762 A1 * | 12/2006 | Schulman et al. | 623/32 |
| 2007/0180858 A1 * | 8/2007 | Wiseman | 63/4 |

OTHER PUBLICATIONS

Merriam-Webster Online Dictionary, Definition of Radial (Radially), accessed Oct. 27, 2010.*

* cited by examiner

*Primary Examiner* — William H. Matthews
*Assistant Examiner* — Marcia Hoffman
(74) *Attorney, Agent, or Firm* — Drinker Biddle & Reath LLP

(57) ABSTRACT

A prosthetic assembly for a residual limb that includes a sleeve for attachment to a distal portion of the residual limb, where the attachment member has a diametrically oriented magnetic field, and a prosthesis with a socket for receiving the sleeve, where the prosthesis socket has a distal end with an attachment member having a corresponding diametrically oriented magnetic field. The diametrically oriented magnetic fields of the sleeve and prosthetic attachment members may be oriented on the prosthesis and the residual limb to achieve a predetermined rotational orientation between the prosthesis and the residual limb and will facilitate removal of the prosthesis with a twisting action.

8 Claims, 6 Drawing Sheets

US 8,206,459 B1

PROSTHETIC-TO-LINER ATTACHMENT MECHANISM

FIELD OF THE INVENTION

This invention pertains generally to devices for attaching a prosthesis to a partially amputated limb and, more particularly, to prosthetic assemblies including a sleeve to be fit to the limb, a prosthesis for receiving the sleeve and limb and interconnecting magnets having alternating face polarity magnetic fields associated with the sleeve and the prosthesis.

BACKGROUND OF THE INVENTION

Suspension sleeves or liners for prosthetic applications are commonly used for attaching a prosthesis to a partially amputated limb. These sleeves or liners are generally made of an elasticized or elastomeric material such as silicone and often include cushioning to minimize discomfort in the residual limb or residuum where it is fitted to a prosthesis.

The sleeves usually have a tubular or "tube sock" shape with an interior a bit smaller than the residual limb to establish a secure seal between the inner surface of the sleeve and the outer surface of the residual limb. In fact, such sleeves preferably provide a generally air-tight seal for removable fixed attachment to the amputee's residual limb and interconnection with a corresponding socket of an orthotic worn by the amputee. Sleeves that may be used are shown, for example, in U.S. Pat. Nos. 4,908,037; 5,830,237; and 6,592,539. Current commercially available sleeves that may be used for this purpose known as "Alpha® Liners" which may be obtained from Ohio Willow Wood of Mt. Sterling, Ohio.

Prosthetic assemblies including sleeves as discussed above are interconnected with appropriate prostheses using a variety of different mechanisms for attaching the prostheses to the sleeves. For example, projecting threaded bolts and corresponding nuts mounted respectively to the sleeve and within the socket are used to thread some prostheses into place. Other much more complex mechanisms are also used. Unfortunately, the currently available attachment mechanisms are less than what is needed in terms of ease of use, reliability, accuracy of attachment, comfort and cost. No current attachment mechanisms are sufficiently simple, accurate and reliable. Since the prostheses are typically repeatedly removed and remounted, ease of removal and replacement is a particular challenge which is not satisfactorily met by current attachment mechanisms.

Accordingly, a simple to use, inexpensive, secure, accurate and easy-to-remove prosthetic attachment mechanism would represent a major advance in the art. The present invention provides a unique attachment mechanism which meets these needs and more.

BRIEF SUMMARY OF THE INVENTION

This invention comprises a prosthetic assembly for a residual limb such as a residua of the humerus, radius/ulna, femur, tibia/fibia, or any of the phalanges. The assembly includes a sleeve for attachment to a distal portion of the residual limb, where the sleeve has a distal end with an attachment member affixed to it. This attachment member has alternating face polarity which may achieved using a single magnet with north and south poles on diametrically opposite sides of a surface of a face of the magnet. Alternatively, alternating face polarity may be achieved using circular groupings of magnets with axially oriented magnetic fields where the poles of each adjacent magnet are offset 180° with respect to its circularly disposed neighbors.

Finally, the prosthesis of the assembly will have a socket sized to receive the distal portion of the residual limb and the sleeve. A corresponding attachment member will be mounted in the distal end of the socket. Again, the attachment member may use a single magnet with a diametrically oriented magnetic field or corresponding circular groupings of magnets with axially oriented magnetic fields where the poles of each adjacent magnet are offset 180° with respect to its circularly disposed neighbors.

The magnetic fields of the corresponding attachment members are oriented on the prosthesis and the residual limb to achieve a predetermined appropriate rotational orientation between the prosthesis and the residual limb when the prosthesis is mounted on the residual limb.

Finally, a flexible member may be applied about the circumference of the prosthesis or about the circumference of the sleeve such that when the user wishes to remove the prosthesis he or she may simply pull upon the flexible member to rotate the attachment members with respect to each other, causing the attachment members to repel, thereby facilitating removal of the prosthesis.

BRIEF DESCRIPTION OF THE DRAWINGS

In order to aid in understanding the invention, it will now be described in connection with exemplary embodiments thereof with reference to the accompanying drawings in which like numerical designations will be given to like features with reference to the accompanying drawings wherein.

DETAILED DESCRIPTION OF THE INVENTION

The embodiment of the invention described in detail below is not intended to be exhaustive or to limit the invention to the precise structure and operation disclosed. Rather, the described embodiment has been chosen and described to explain the principles of the invention and its application, operation and use in order to best enable others skilled in the art to follow its teachings.

Figure 1:
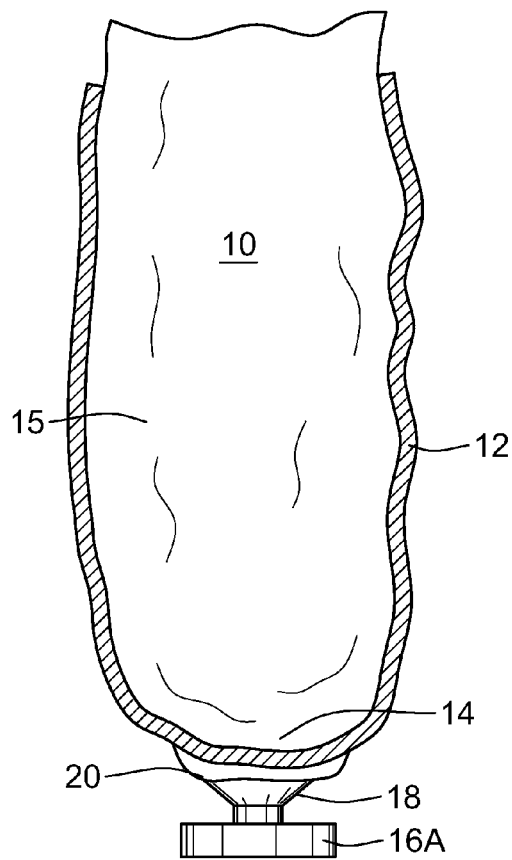
FIG. 1 depicts a portion of an example of a residual limb with a suspension sleeve tightly fitted to the residual limb.

Turning now to FIG. 1, a portion of a residual limb 10 is depicted, with a suspension sleeve 12 tightly fitted to the residual limb. The sleeve may be applied, for example, by first rolling it up, then positioning the open end of the rolled-up sleeve opposite the distal end 14 of the residual limb, and then rolling the sleeve onto the distal portion 15 of the residual limb.

A disk magnet 16A with a diametrically oriented magnetic field, such as one made of neodymium (NdFeB) available from K & J Magnetics of Jamison, Pa., is affixed to a fixture 18 at the proximal outer surface 20 of the sleeve. The disk magnet has north and south poles on diametrically opposite sides of a surface of a face of the magnet, as shown. This magnetic field configuration may also be referred to as an "alternating face polarity field". The fixture may be permanently attached to the sleeve with adhesive or other appropriate attachment means. Alternatively, commercially available liners are available with fixtures already rigidly attached to the sleeve. Magnet 16A may be permanently affixed to the fixture with adhesive or with a conventional rivet, screw and nut pair, or other attachment means. Also, while the disk shape is preferred, the magnets with such diametrically opposite magnetic fields or alternating face polarity fields may be of any available geometric shape.

Figure 2:
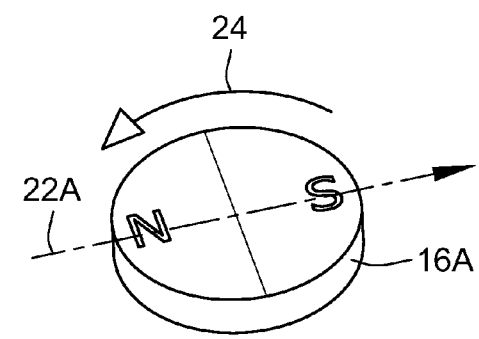
FIG. 2 depicts a pair of disk magnets with diametrically oriented magnetic fields positioned opposite each other where the magnets are oriented south pole-to-north pole so that the magnets attract.
Figure 2:
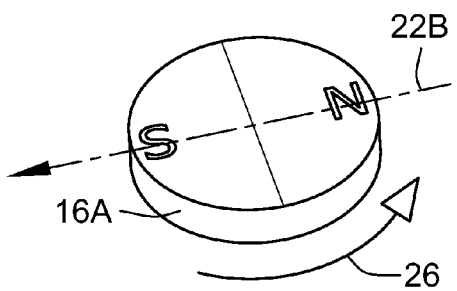

Magnet 16A is shown in FIG. 2 with its diametrically oriented magnetic field 22A indicated diagrammatically in the figure. A corresponding disk magnet 16B with a like diametrically oriented magnetic field 22B is also shown in this figure. When free to find a rest state, the two magnets will be oriented with their respective diametrically oriented magnetic fields south pole-to-north pole and the magnets attracted together by their opposing magnetic poles. Since the magnets are axially aligned, rotation of magnet 16A with respect to magnet 16B more than 90 degrees in directions 24 or 26 will cause the magnetic fields of the opposing magnets to repel. This repelling force begins as soon as the aligned magnetic fields begin to be displaced circumferentially (i.e., by rotation) and increases in force (at a given axial alignment and separation between the magnets) as the relative circumferential displacement of the corresponding magnetic fields about their common axis is increased.

Figure 3A:
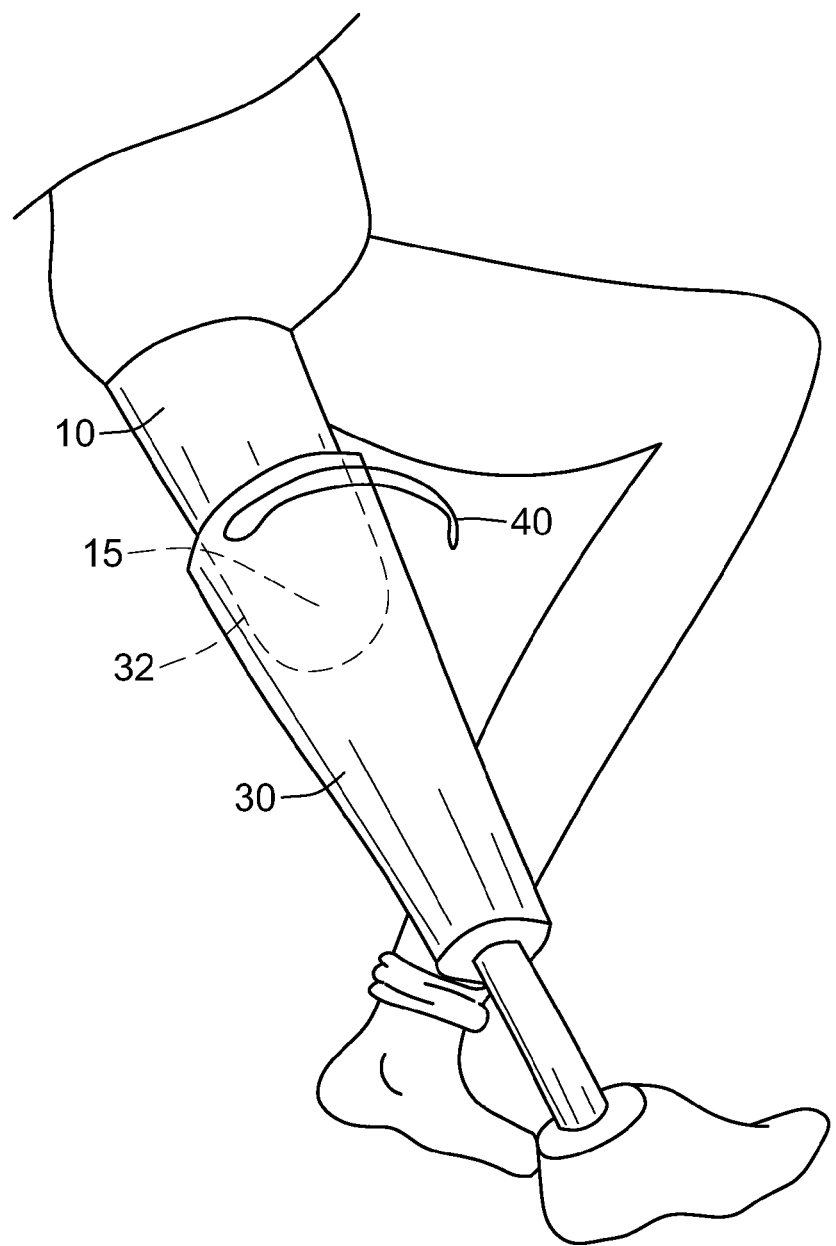
FIGS. 3A-3C depict respectively a prosthesis mounted to a residual limb, a portion of the residual limb juxtaposed opposite the socket of the prosthesis before complete mounting and the socket of the prosthesis mounted over the residual limb.
Figure 3B:
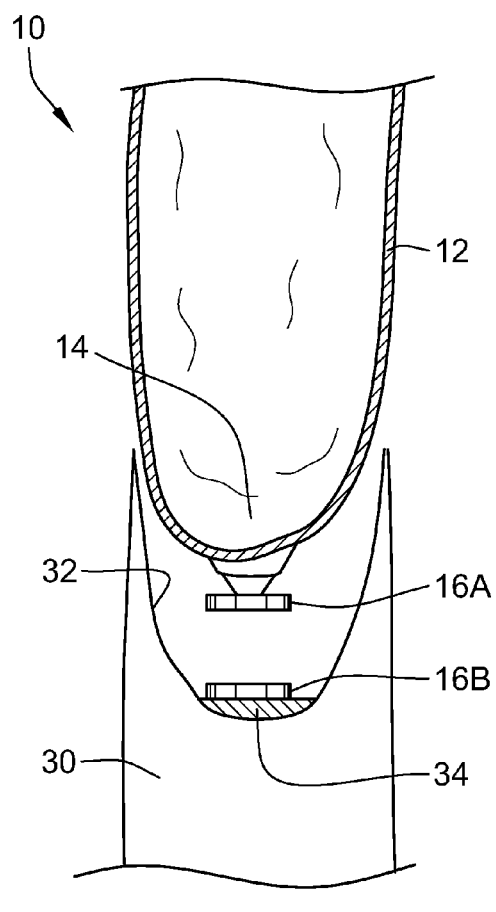
Figure 3C:
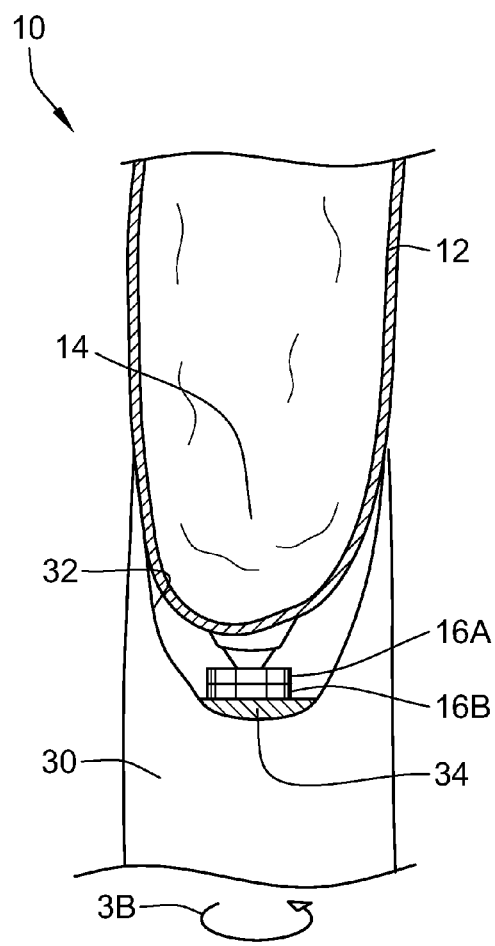

Turning now to FIGS. 3A, 3B and 3C, a prosthetic leg 30 is shown having a concave socket 32 for receiving a distal portion 15 of residual limb 10. (The connection, of course, has equal application to any other prosthesis that is attached to a prosthetic limb including, for example, prosthetic arms.) Magnet 16B is mounted at the distal end 34 of the prosthesis socket. Magnet 16A is mounted to the distal end of sleeve 12 as discussed above with respect to FIG. 1. Thus, when the prosthesis is moved into position on the sleeve with magnets 16A and 16B close enough to each other to achieve magnetic attraction between the two magnets (FIG. 3B), magnet 16B will rotate to align its magnetic fields north pole-to-south pole with magnet 16A as the prosthesis is drawn into a fixed position over the sleeve by magnetic attraction as shown in FIG. 3C.

Figure 4:
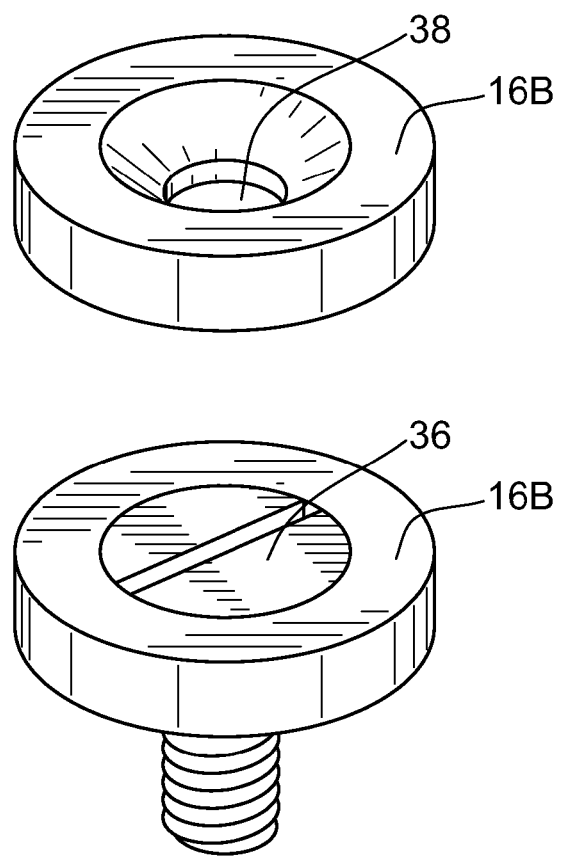
FIG. 4 contains two views of a disk magnet with a diametrically oriented magnetic field for use in the invention, in which a bore passes through the center of the magnet and a screw is positioned in the bore.

Magnet 16B preferably will be previously oriented in the socket to ensure proper positioning of the prosthesis with respect to the residual limb. In one preferred embodiment, magnet 16B may be affixed as shown in FIG. 4 by a screw 36 passing through a bore 38 at the center of the magnet. This screw may be loosened to permit adjustment of the circumferential orientation of the prosthesis and then tightened in place once the desired orientation is achieved to ensure that whenever the prosthesis is removed and replaced, it will return to the desired orientation.

Once in place, the prosthesis will be firmly but removably fixed onto the sleeve and the residual limb by the magnetic attraction between magnets 16A and 16B. Thus, when the amputee wishes to remove the prosthesis, he or she need only rotate the prosthesis slightly (just passing 90 degrees in the case of the single, centered magnet) as indicated by arrow 38 in FIG. 3C to move the diametrically oriented magnetic fields of magnets 16A and 16B sufficiently out of alignment to cause the two magnets to repel each other thereby initiating and facilitating removal of the prosthesis from the residual limb.

Additionally, a flexible member 40 (FIG. 3) may be applied to the circumference of the prosthesis to facilitate rotation of the prosthesis by the user to achieve removal as discussed above. Alternatively, such a flexible member may be connected to the sleeve and passed through a hole or slit in the prosthesis socket. In this case, the rotation of the sleeve and soft tissue "inside" the socket may be enough to cause the opposing magnets to repel to facilitate removal of the prosthesis. Thus, in either case when the user wishes to remove the prosthesis he or she need only pull on the flexible member.

Figure 5:
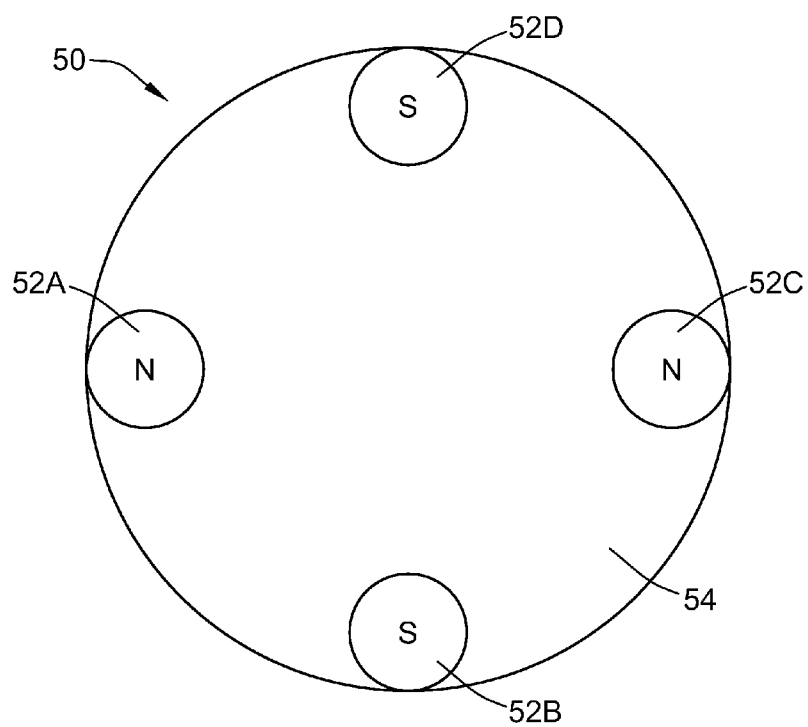
FIG. 5 illustrates an alternative magnet configuration in which a grouping of alternating face polarity magnets is circularly disposed about the circumference of a generally planar supporting disk which may be used in lieu of the magnets with diametrically oriented magnetic fields shown and used in the embodiments of FIGS. 1-4.

FIG. 5 illustrates an alternative embodiment of the invention in which an alternating face polarity field is established with a circular grouping 50 of magnets 52A-52D arranged about the circumference of a generally coplanar disk 54. In a less preferred embodiment, this coplanar circularly arranged grouping of magnets may be used in lieu of either one of magnets 16A and 16B discussed above, provided the circumference of the single magnet (16A or 16B) is large enough to capture the ring of cooperating magnets. The magnets with axially oriented magnetic fields preferably will be mounted onto their respective disks or other generally planar member which in turn will be attached, respectively, to the proximal end of the sleeve and mounted within the distal end of the socket.

Grouping 50 will comprise at least two magnets with axially oriented magnetic fields where the poles of each adjacent magnet are offset 180° with respect to its adjacent magnets, or "neighbors". The numbers of magnets preferably will be even and may comprise as few as two magnets, but preferably will include at least 4 magnets up to any desired even number. An odd number of magnets could be used but would not be ideal since the rotation-to-release would mean that all but one of the similar poled magnets are rotated over each other, causing a net repulsion effect but with a small point of attraction. Also, the magnets can be arranged in other non-circular geometric configurations where the poles of adjacent circularly disposed magnets are offset 180° with respect to their adjacent magnets.

Figure 6A:
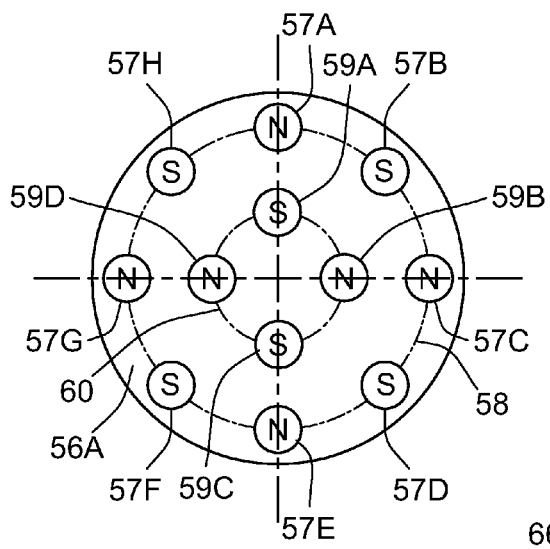
FIGS. 6A-6C illustrate other alternative magnet configurations of circularly disposed groupings of alternating face polarity magnets.
Figure 6B:
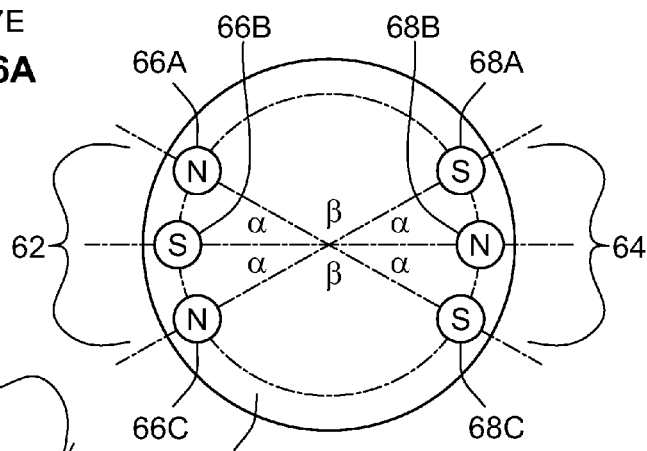
Figure 6C:
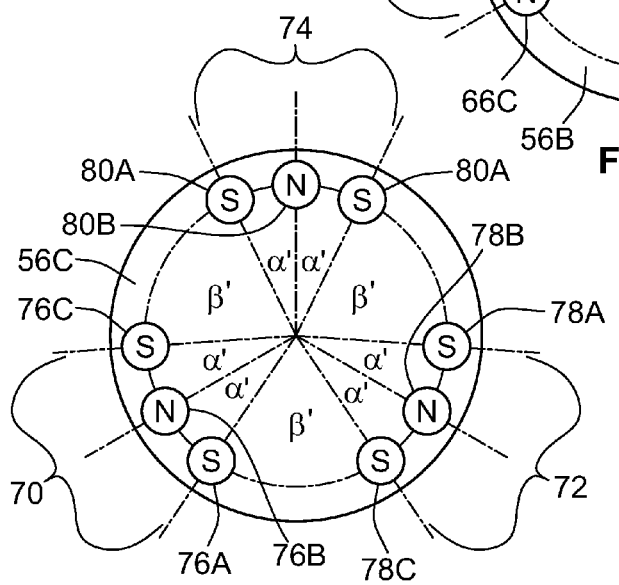

For example, FIGS. 6A-6C illustrate three alternative magnet configurations that could be used. In each of these cases the magnets are shown mounted, respectively, on disk 56A, 56B and 56C. Thus, in FIG. 6A magnets 57A-57H are arranged in circle 58 and magnets 59A-59D are arranged in circle 60. The circularly disposed magnets in each circle have axially oriented magnetic fields with the poles of each adjacent magnet offset 180° with respect to its adjacent circularly disposed magnets. Also, preferably, magnets in the two circles are located coaxially as shown. Any number of rings may be used. The corresponding plate of the sleeve or the prosthesis would have the magnets arranged in the same fashion.

FIG. 6B illustrates a magnet configuration in which a series of two groupings 62 and 64 of circularly arranged axial magnets 66A-66C and 68A-68C are positioned on disk 56 parallel to the circumference of the disk. Again, the poles of the adjacent magnets in each grouping are offset 180 degrees with respect to their circularly disposed adjacent magnets. Additionally, it is preferred that the spacing of the magnets be uniform such that all angles $\alpha$ are all equal and all angles $\beta$ are equal.

Figure 7B:
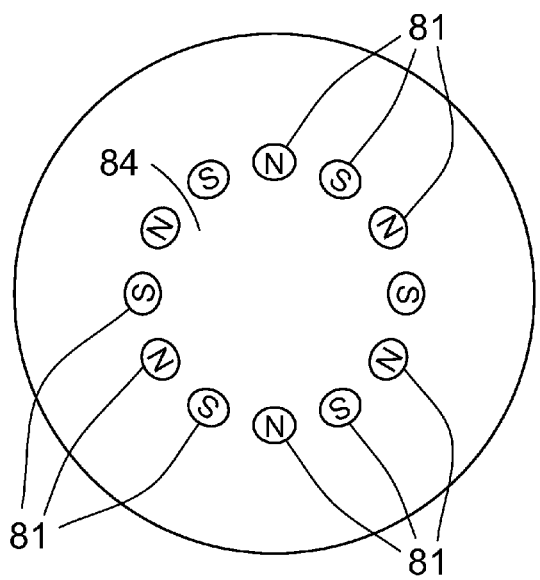
FIGS. 7A and 7B depict yet another alternative embodiment of the invention in which disk magnets with diametrically oriented magnetic fields are positioned in a non-coplanar fashion by attachment to the outer surface of the sleeve on the residual limb and the inner surface of the socket of the prosthesis.
Figure 7A:
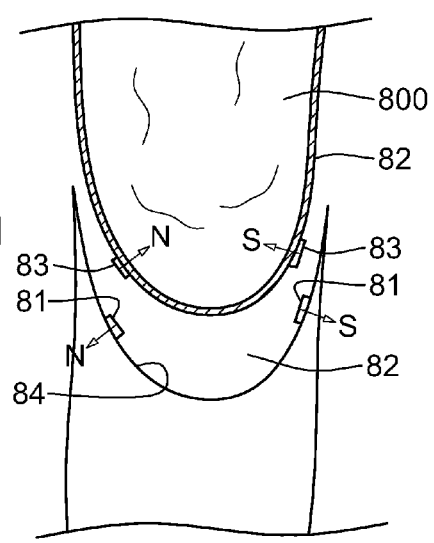

FIG. 6C illustrates another magnet configuration. In this configuration three groupings 70, 72 and 74 of axially disposed magnets 76A-76C, 78A-78C and 80A-80C are mounted on disk 56 with the groupings equally spaced apart by the angle $\beta'$ and the magnets in each grouping equally spaced apart by the angle $\alpha'$ FIG. 7A illustrates yet another embodiment of this invention. In this embodiment, magnets 81-83 may be mounted in groupings directly to the outer surface 82 of sleeve 80 and the inner surface 84 of prosthesis socket 82, as shown. Preferably the groupings will be circular so that, for example, when socket 82 is viewed from the end, magnets 81 will appear generally as depicted in FIG. 7B. As a result, the socket of the prosthesis will be drawn onto the sleeve in the desired orientation as described above with respect to the embodiment of FIGS. 1-4 and will be readily released by rotating the prosthesis with respect to the sleeve to cause the respective magnet groupings of the sleeve and prosthesis to repel.

Finally, it is noted that the amount of rotation needed to release is related to the magnets' configuration. For example, the expected amount of rotation needed to release the arrangement in FIG. 6B is greater than at least α/2 in either direction, the arrangement of FIG. 5 is expected to require rotation of greater than at least 45 degrees, and the arrangement of FIG. 6A is expected to require rotation of greater than at least 22.5 degrees.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A prosthetic assembly for attachment to a residual limb comprising:
    a sleeve for attachment to a distal portion of the residual limb, the sleeve having a distal end with an attachment member affixed thereto, where the attachment member is a magnet with a diametrically oriented magnetic field consisting of north and south poles on diametrically opposite sides of a surface of a face of the magnet; and
    a prosthesis having a socket sized to receive the distal portion of the residual limb and the sleeve, the prosthesis socket having a distal end with an attachment member affixed thereto, where the attachment member is a magnet with a diametrically oriented magnetic field consisting of north and south poles on diametrically opposite sides of a surface of a face of the magnet,
    the sleeve being fixed within the socket of the prosthesis with the attachment members in sufficiently close proximity to retain the prosthesis on the sleeve by magnetic attraction and to detach the prosthesis by rotating it vis-à-vis the attachment member of the sleeve to cause the attachment members to repel each other,
    in which the diametrically oriented magnetic fields of the attachment members are oriented respectively on the prosthesis and the residual limb sleeve to achieve a predetermined rotational orientation between the prosthesis and the residual limb sleeve.

2. The prosthetic assembly of claim 1 in which the sleeve is a suspension sleeve.

3. The prosthetic assembly of claim 1 in which the attachment members are disk-shaped magnets.

4. The prosthetic assembly of claim 3 in which the magnets are made of neodymium.

5. The prosthetic assembly of claim 1 in which the prosthesis includes a flexible member generally radially affixed to the outer surface of the prosthesis for rotating the attachment member of the prosthesis vis-à-vis the attachment member of the residual limb sleeve causing the attachment members to repel each other thereby releasing the prosthesis from the sleeve.

6. A prosthetic assembly for achieving a predetermined rotational orientation between a prosthesis and a residual limb sleeve and for facilitating removal of the prosthesis by rotating it relative to the sleeve comprising:
    a suspension sleeve for attachment to a distal portion of the residual limb, the sleeve having a distal end with an attachment member affixed thereto, the attachment member having a diametrically oriented magnetic field;
    a prosthesis having a socket sized to receive the distal portion of the residual limb and the sleeve, the prosthesis socket having a distal end with an attachment member affixed thereto, the attachment member having a corresponding diametrically oriented magnetic field;
    the diametrically oriented magnetic fields of the attachment members are oriented on the prosthesis and the sleeve to achieve a predetermined rotational orientation between the prosthesis and the sleeve and to detach the prosthesis by rotating it vis-à-vis the attachment member of the sleeve to cause the attachment members to repel each other; and
    a flexible member generally radially affixed to the outer surface of the prosthesis for rotating the attachment member of the prosthesis vis-à-vis the attachment member of the residual limb sleeve causing the attachment members to repel each other thereby releasing the prosthesis from the sleeve.

7. The prosthetic assembly of claim 6 in which each attachment member comprise a plurality of circularly arranged generally coplanar magnets with axially oriented magnetic fields and the poles of each successive magnet offset 180° from the poles of its two circularly adjacent magnets.

8. The prosthetic assembly of claim 7 in which the magnets are not coplanar and are attached to the surface of the sleeve and the prosthesis socket.

* * * * *